(12) United States Patent
Rice et al.

(10) Patent No.: US 7,439,410 B1
(45) Date of Patent: Oct. 21, 2008

(54) INTEGRATED ALKYLATION-ISOMERIZATION PROCESS

(75) Inventors: Lynn H. Rice, Arlington Heights, IL (US); Dale J. Shields, Grayslake, IL (US)

(73) Assignee: UOP LLC, Des Plaines, IL (US)

( * ) Notice: Subject to any disclaimer, the term of this patent is extended or adjusted under 35 U.S.C. 154(b) by 52 days.

(21) Appl. No.: 11/694,508

(22) Filed: Mar. 30, 2007

(51) Int. Cl.
*C07C 2/56* (2006.01)
*C07C 5/27* (2006.01)

(52) U.S. Cl. ............... 585/332; 585/331; 585/734; 585/709

(58) Field of Classification Search ......... 585/331, 585/332, 734, 709
See application file for complete search history.

(56) References Cited

U.S. PATENT DOCUMENTS

| 4,324,937 | A | 4/1982 | Vora | 585/315 |
| 5,672,798 | A | 9/1997 | Zhang et al. | 585/467 |
| 6,172,274 | B1 | 1/2001 | Gosling | 585/446 |
| 6,392,114 | B1 | 5/2002 | Shields et al. | 585/719 |

OTHER PUBLICATIONS

Robert A. Meyers, *Handbook of Petroleum Refining Processes*, Second Edition, McGraw-Hill, New York, 1997, Chapters 1.1, 1.4 and 9.2.
Cara M. Roeseler, et al., "*Improved Solid Catalyst Alkylation Technology for Clean Fuels: The Alkylene Process*", 2002.

*Primary Examiner*—Thuan Dinh Dang
(74) *Attorney, Agent, or Firm*—Maryann Maas (57) ABSTRACT

An integrated isomerization-alkylation process is disclosed that uses a common distillation zone. The process can comprise halogen removal. The process is suitable for the production of motor fuels from isoparaffins and olefins using solid alkylation and isomerization catalysts.

20 Claims, 5 Drawing Sheets

FIG 6

INTEGRATED ALKYLATION-ISOMERIZATION PROCESS

FIELD OF THE INVENTION

This invention relates to the alkylation of hydrocarbons to produce useful chemicals and motor fuel. This invention specifically relates to a process for producing motor fuel blending components by isomerizing normal paraffins and by alkylating the isoparaffins with olefins using a solid catalyst.

BACKGROUND OF THE INVENTION

Hydrocarbon alkylation is widely used in the petroleum refining industry. It is used to make a variety of useful acyclic hydrocarbon products. These products are consumed in motor fuel and as petrochemical feedstocks.

Alkylation comprises reacting two feedstocks, an alkylation substrate and an alkylation agent. To produce motor fuels, the alkylation substrate is an isoparaffin, commonly isobutane, and the alkylation agent is an olefin, usually propylene or butenes. Large amounts of paraffins for high-octane gasoline are made by alkylating isobutane with propylene or butenes in large-scale commercial facilities. Liquid phase hydrofluoric acid (HF) or sulfuric acid is often used as the catalyst. Because liquid acids are volatile and the environmental risks arising from an accidental release to the atmosphere are more and more undesirable, solid catalysts have been proposed for alkylation to produce motor fuels.

Isomerization of normal paraffins is widely used in the petroleum refining industry. Butane isomerization is integrated with alkylation in multi-step processes to increase butane utilization. The normal butanes are isomerized and the resultant isobutane is consumed in the alkylation reaction with olefins. Such processes are described in U.S. Pat. No. 4,324,937 and in Chapter 9.2 of the book titled Handbook of Petroleum Refining Processes, edited by Robert A. Meyers, Second Edition, McGraw-Hill, New York, 1997, ISBN 0-07-041796-2 (hereinafter, Handbook). The debutanizer distillation column of the integrated process is commonly called an isostripper since it produces an overhead for recovering isobutane and a side draw for separately recovering normal butane. (In contrast, where the debutanizer distillation zone has no separate side draw for normal butane and instead recovers isobutane and normal butane together in one or more overhead streams, then the debutanizer distillation zone is commonly called a debutanizer.) The side draw has a suitably high normal butane content so that it can be combined with makeup hydrogen, heated, and charged to the isomerization reactor. The isomerization reaction zone effluent is cooled and passes to a distillation column commonly called a stabilizer. The stabilizer overhead is a light gas byproduct. The stabilizer bottoms stream contains isobutane and passes to the isostripper, where any isobutane is recovered in the isostripper overhead and flows to the alkylation reactor. Any unconverted normal butane is recovered in the isostripper's side draw for return to the isomerization reactor. Any heavier hydrocarbons in the stabilizer bottoms stream are recovered in the isostripper bottoms stream.

Economical and efficient ways are sought to improve the integration of alkylation and isomerization processes.

INFORMATION DISCLOSURE

Chapters 1.1 and 1.4 of the Handbook describe alkylation processes that use sulfuric acid or HF catalyst. U.S. Pat. No. 5,672,798; U.S. Pat. No. 6,172,274 B1; and U.S. Pat. No. 6,392,114 B1, which are hereby incorporated herein in their entireties, describe alkylation processes that use a solid catalyst.

Chapter 9.2 of the Handbook describes a process for the isomerization of normal paraffins. U.S. Pat. No. 4,324,937, Chapter 9.2 of the Handbook, and the paper titled "Improved Solid Catalyst Alkylation Technology for Clean Fuels: The Alkylene Process", by Cara M. Roeseler, et al., paper no. AM-02-17, presented at the 2002 NPRA Annual Meeting, Mar. 17-10, 2002, in San Antonio, Tex., U.S.A. describe processes which isomerize normal butanes and consume the resultant isobutane in an alkylation reaction with olefins.

BRIEF SUMMARY OF THE INVENTION

An alkylation-isomerization process is disclosed herein that uses a common distillation column zone to remove propane and lower-boiling components that are present in both the alkylation and isomerization reaction zone effluents. The process can prevent unacceptable accumulations of these components in the alkylation reactor. The process efficiently integrates equipment, which can reduce capital and/or operating costs. For example, in one embodiment the stabilizer distillation column used in conventional alkylation-isomerization processes can be eliminated.

The process disclosed herein is useful where the alkylation and isomerization reaction zone effluents can be combined to form a mixture without significant adverse consequences. Such consequences typically may be undesirable contamination of the product, reactions between the components, condensation or precipitation of salts or deposits, or corrosion of equipment. The process disclosed herein is particularly useful where the light components and/or byproducts in both the alkylation and isomerization effluents can be combined to form a stream without significant adverse consequences. Examples of light components typically include hydrogen chloride, $C_3$ and lighter hydrocarbons and molecular hydrogen. For example, where both the alkylation and isomerization reactors use chloride-containing or chloride-promoted catalysts, their respective effluents can contain significant concentrations of hydrogen chloride. In the process disclosed herein, streams containing these light components can be combined and processed together. These streams may contain little or no water, if water can increase the potential for catalyst deactivation and/or corrosion.

In one embodiment, $C_3$ and lighter hydrocarbons in the alkylation and isomerization reaction zone effluents can be separate from isobutane in a distillation zone and the isobutane is recycled. In another embodiment, hydrogen chloride in either or both of the alkylation and isomerization effluents can be reacted with an olefin to form a chloroparaffin, which can be recycled to the alkylation reactor to increase chloride utilization. In yet another embodiment, the isomerization reaction zone effluent passes to a flash drum, which concentrates the hydrogen chloride in a stream to be reacted with the olefin.

DETAILED DESCRIPTION OF THE INVENTION

An alkylation agent and a normal paraffin are fed from external sources to the process disclosed herein. The alkylation agent is an olefin having 3 or 4 carbon atoms per molecule, sometimes referred to herein as a $C_3$-$C_4$ olefin. The $C_3$-$C_4$ olefin is preferably a monoolefin and commonly one or more of the butenes. The alkylation agent is typically derived from cracking or dehydrogenation process units in a petroleum refinery. A feedstock for the process disclosed herein that contains the alkylation agent may contain other components, such as propane. The feedstock may have been treated to remove sulfur, water, nitrogen, and/or diolefins by conventional techniques.

The normal paraffin fed to the process is typically capable of being isomerized into an isoparaffin having the same number of carbon atoms per molecule and which is typical alkylation substrate for the alkylation agent. Preferably, the normal paraffin is normal butane and the isoparaffin is isobutane. The source of the normal paraffin is typically fractionation or liquefaction of gaseous or normally liquid petroleum stocks, field butanes, and synthetic paraffins such as from Fischer-Tropsch processes, cracking of higher molecular weight hydrocarbons, and the like. The composition of the normal paraffin-containing feed will depend upon its source. Normal paraffin-containing feeds may contain from about 30 to about 100 wt-% normal paraffin. The balance of the feed may be corresponding isoparaffins. Monoolefins may also be present but preferably their concentration is low or nil. If present in the normal paraffin-containing feed, hydrocarbons lighter than the normal paraffin have a concentration of less than about 20, preferably less than about 5, wt-% and hydrocarbons heavier than the normal paraffin have a concentration of less than about 10, preferably less than about 5, wt-%. The concentration of $C_6$ or heavier hydrocarbons in the normal paraffin-containing feed can be reduced by distillation in a deisobutanizer so that the concentration of $C_6$ and heavier hydrocarbons in the stream fed to the isomerization reactor is less than 1, preferably less than about 0.5, wt-%. The normal paraffin-containing feedstock may have been treated to remove sulfur, water, nitrogen, and/or diolefins by conventional techniques. Although not preferred, the normal paraffin-containing feedstock may also contain normal pentane, which can be isomerized to some extent in the isomerization reaction zone to isopentane, which in turn can be passed to the alkylation reaction zone and alkylated to some extent with the $C_3$-$C_4$ olefin.

Figure 1:
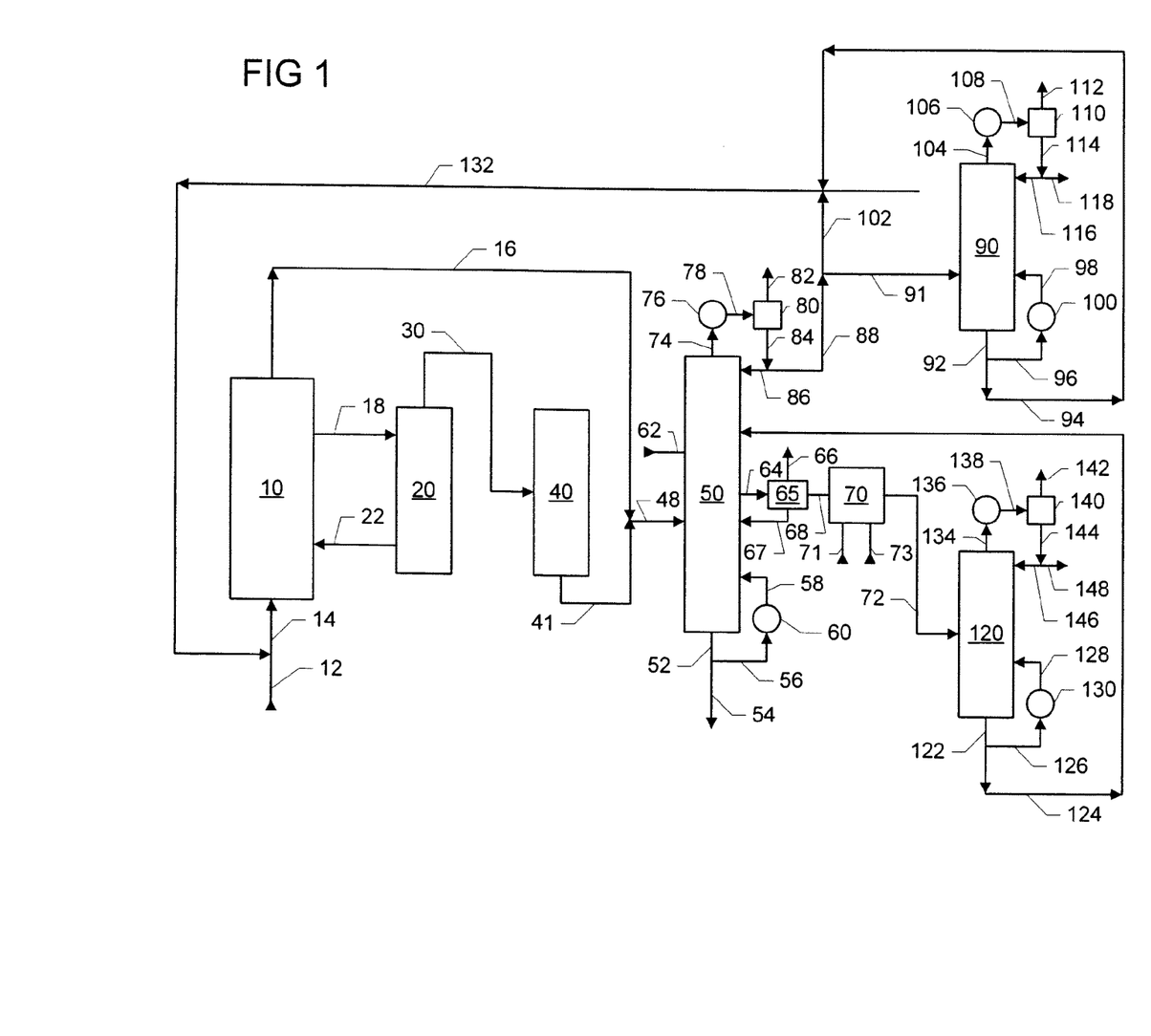
FIG. 1 is a schematic drawing of a conventional process.

In order to illustrate the efficiently integrated alkylation-isomerization process disclosed herein, a conventional alkylation-isomerization process shown in FIG. 1 having non-integrated depropanizer and stabilizer distillation zones is first described. FIGS. 1-12 are schematic representation of processes and show only the portions of major equipment necessary to understand each process. For clarity and simplicity some items associated with the operation of the processes have not been shown. These items include flow and pressure control valves, heaters, pumps, compressors, heat exchangers, temperature and pressure monitoring systems, vessel internals, etc., which may be of customary design. In addition, the description of FIGS. 1-12 that follows is written in terms of normal butane isomerizing to isobutane, butene alkylating isobutane, and both isomerization and alkylation taking place in the presence of chloride-containing catalysts. However, the choice of these particular reactants and catalysts is not intended to limit the scope of the invention as set forth in the claims.

Referring to FIG. 1, a butene-containing feedstock from a fluid catalytic cracking (FCC) process unit flows through line 12 and combines with a recycle stream in line 132 that contains mainly isobutane. The combined stream of reactants enters alkylation riser-reactor assembly 10 via line 14. Reactor assembly 10 can be of the type described in U.S. Pat. No. 5,672,798; U.S. Pat. No. 6,172,274 B1; and U.S. Pat. No. 6,392,114 B1. The reactants contact an alkylation catalyst and flow upward through the riser-reactor. In the riser-reactor butenes are consumed by reacting with isobutane supplied in excess to produce alkylate. The alkylation reaction zone effluent contains alkylate, isobutane, propane, hydrogen chloride, and possibly unreacted propylene, molecular hydrogen, and light byproducts of side reactions such as methane and ethane. These components are separated by density difference from the catalyst. Alkylation reaction zone effluent passes through line 16 and flows via line 48 to isostripper distillation column 50.

Spent catalyst exiting assembly 10 typically contains deposits that can cause catalyst deactivation. If catalyst reactivation is desired, spent catalyst may pass via line 18 to optional alkylation catalyst reactivator 20. Optional reactivator 20 can be of the type described in U.S. Pat. No. 5,672,798; U.S. Pat. No. 6,172,274 B1; and U.S. Pat. No. 6,392,114 B1. Although not shown in the drawing, molecular hydrogen and isobutane may be introduced to optional reactivator 20 to reactivate the catalyst. Reactivated catalyst passes to assembly 10 via line 22. A reactivator effluent containing isobutane, heavier materials removed from spent catalyst, and possibly molecular hydrogen and hydrogen chloride may pass via line 30 to optional reactivation stripper 40. Optional stripper 40 can be of the type described in U.S. Pat. No. 5,672,798; U.S. Pat. No. 6,172,274 B1; and U.S. Pat. No. 6,392,114 B1. The heavier materials can exit optional stripper 40 in a stripper bottoms stream and flow through lines 41 and 48 to isostripper distillation column 50.

Field butanes containing normal butane and isobutane enter isostripper 50 via line 62. A side draw containing normal butane flows via line 64 to rectifier distillation column 65 to remove any hydrocarbons having more than four carbon atoms per molecule. The rectifier concentrates these heavier hydrocarbons in the rectifier bottoms stream for return to isostripper 50 via line 67 while normal butane concentrates in the rectifier overhead. Some of the rectifier overhead exits through line 66 to prevent normal butane from accumulating to unacceptable levels in the process, and the remainder flows through line 68 to isomerization reactor assembly 70. Makeup hydrogen enters assembly 70 via line 71 and makeup organic chloride enters via line 73. A combined stream of normal butane, hydrogen, and organic chloride at the desired inlet temperature contacts isomerization catalyst in reactor 70.

The isomerization reaction zone effluent contains a near-equilibrium distribution of normal butane and isobutane, and it also contains propane, ethane, methane, hydrogen, and hydrogen chloride. The effluent flows through line 72 and enters stabilizer distillation column 120. The stabilizer overhead flows via line 134 to condenser 136 and then via line 138 to receiver 140 for phase separation. Overhead gas containing hydrogen and hydrogen chloride from receiver 140 flows via line 142 to conventional gas scrubbers. A portion of propane-containing overhead liquid in line 144 is refluxed via line 146 to stabilizer 120 and the rest passes via line 148 to conventional saturated gas recovery facilities. The bottoms stream from stabilizer 120 contains normal butane and isobutane and flows through line 122. A portion of the bottoms stream passes via line 126 to reboiler 130, and the reboiled stream returns to stabilizer 120 via line 128. Another portion of the bottoms stream flows via line 124 to isostripper 50.

The bottoms stream of isostripper 50 contains alkylate and other heavy components and flows through line 52. A portion of the bottoms stream is product that is typically sent via line 54 to conventional facilities for chloride removal and/or gasoline blending. Another portion of the bottoms stream passes via line 56 to reboiler 60, where the stream is heated and then passed via line 58 to isostripper 50. The isostripper overhead in line 74 contains isobutane, lighter hydrocarbons such as propane and ethane, and hydrogen chloride. The isostripper overhead flows via line 74 to condenser 76 and then via line 78 to receiver 80 for phase separation. Overhead gas containing hydrocarbons lighter than propane and possibly hydrogen chloride from receiver 80 flows via line 82 to conventional gas scrubbers. Overhead liquid collected from receiver 80 in line 84 contains propane, isobutane, and possibly hydrogen chloride. A portion of the overhead liquid serves as reflux and flows via line 86 to isostripper 50. A second, larger portion of the overhead liquid in line 88 flows via line 102 and combines with the isobutane-containing net depropanizer bottoms stream in line 94 to form the recycle stream in line 132. The recycle stream contains mainly isobutane but can also contain propane and possibly hydrogen chloride.

While most of the overhead liquid is recycled to the alkylation reactor assembly 10, a slip stream of overhead liquid passes via line 91 to depropanizer distillation column 90 to prevent propane and lighter hydrocarbons from accumulating to unacceptable levels in the process. The depropanizer overhead flows via line 104 to condenser 106 and then via line 108 to receiver 110 for phase separation. Overhead gas containing propane and lighter hydrocarbons from receiver 110 flows via line 112 to conventional gas scrubbers. A portion of propane-containing overhead liquid in line 114 is refluxed via line 116 to depropanizer 90 and the rest passes via line 118 to conventional saturated gas recovery facilities. The bottoms stream from depropanizer 90 contains isobutane and flows through line 92. A portion of the bottoms stream passes via line 96 to reboiler 100, and the reboiled stream returns to depropanizer 90 via line 98. Another portion of the bottoms stream flows via line 94 for recycle to the alkylation reactor assembly 10.

FIGS. 2 to 13 show embodiments of the process disclosed herein that do not employ the stabilizer 120 shown in FIG. 1. Items in FIGS. 2 to 13 having the same or similar function as items in FIG. 1 have the same item numbers, only the portion of the embodiments necessary to understand the differences from the process shown in FIG. 1 are shown in FIGS. 2 to 13, and the description of FIGS. 2 to 13 that follows mainly focuses on those differences.

Figure 2:
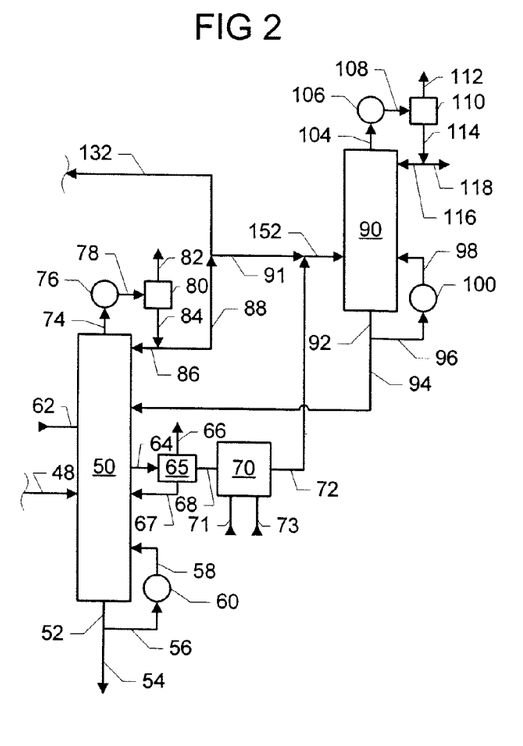
FIGS. 2-13 are schematic drawings of embodiments of the process disclosed herein.

The embodiments in FIGS. 2 to 7 do not use an alkylation reaction zone effluent flash. In FIG. 2, the isomerization reaction zone effluent flows to depropanizer 90 instead of to stabilizer 120. The isomerization reaction zone effluent in line 72 combines with the slip stream in line 91 to form a stream fed via line 152 to depropanizer 90. The net depropanizer bottoms stream in line 94 passes to isostripper 50 instead of combining with a portion of the isostripper overhead liquid.

The embodiments in FIGS. 3 to 7 use a chloride treater 150. Chloride treater 150 can contain any suitable contacting medium such as glass beads or any mild acid function catalyst such as alumina to catalyze the reaction of the olefins and hydrogen chloride to form chloroparaffins (e.g., chloropropane or chlorobutane). The contacting medium or catalyst in chloride treater 150 is maintained in a fixed bed. Treating conditions depend on the specific nature of the contacting medium or catalyst, but can include ambient temperature and pressures above atmospheric pressure. The treating pressure may be higher than that of depropanizer 90 and lower than that of reactor 70 and may be in the range of from about 1724 kPa(g) (250 psi(g)) to about 2758 kpa(g) (400 psi(g)). Suitable chloride treaters are conventional and well known.

Figure 3:
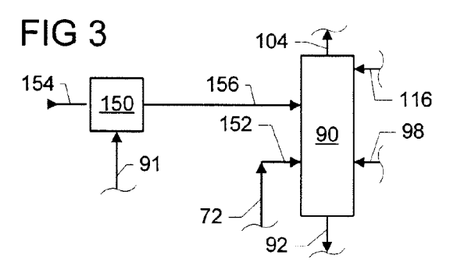

FIG. 3 shows a variation of FIG. 2. The isostripper overhead liquid containing hydrogen chloride in line 91 flows to chloride treater 150. An olefin-containing stream in line 154 containing a mixture of propylene and butenes, or preferably butenes, or less commonly propylene is also fed to chloride treater 150. In chloride treater 150 the olefins are consumed by reaction with hydrogen chloride at conditions sufficient to form chloroparaffins, such as chloropropane, 1-chlorobutane, 2-chlorobutane, 1-chloro-2-methylpropane, and 2-chlor-2-methylpropane. A treater effluent stream containing chloroparaffins and propane and lighter paraffins passes via line 156 to depropanizer 90. The chloroparaffins tend to concentrate with isobutane in the bottom of depropanizer 90 and are carried in the net depropanizer bottoms stream via line 94 to isostripper 50. In isostripper 50 the chloroparaffins tend to concentrate with isobutane in the overhead liquid and are recycled to the alkylation reactor assembly 10 via lines 88 and 132.

Figure 4:
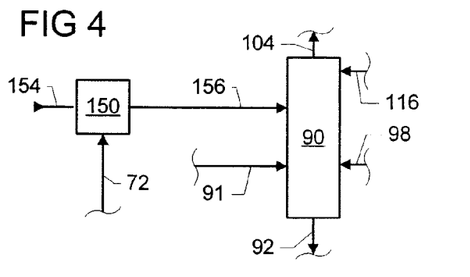
Figure 5:
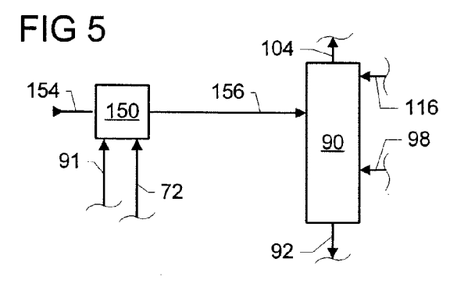

FIG. 4 shows another variation of FIG. 2. The isomerization reaction zone effluent in line 72, rather than the isostripper overhead liquid as in FIG. 3, flows to chloride treater 150. Hydrogen chloride in the isomerization reaction zone effluent reacts with the olefins in chloride treater 150. The treater effluent stream in line 156 contains chloroparaffins, normal butane, isobutane, and other light hydrocarbons and passes via line 156 to depropanizer 90. FIG. 5 shows yet another variation of FIG. 2 in which both the isostripper overhead liquid in line 91 and the isomerization reaction zone effluent in line 72 flow to chloride treater 150.

Figure 6:
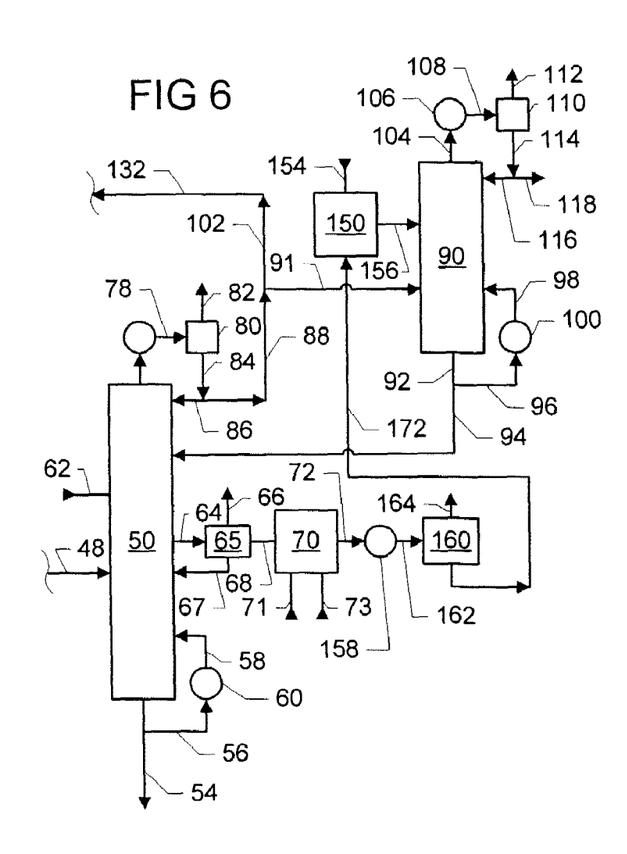
Figure 7:
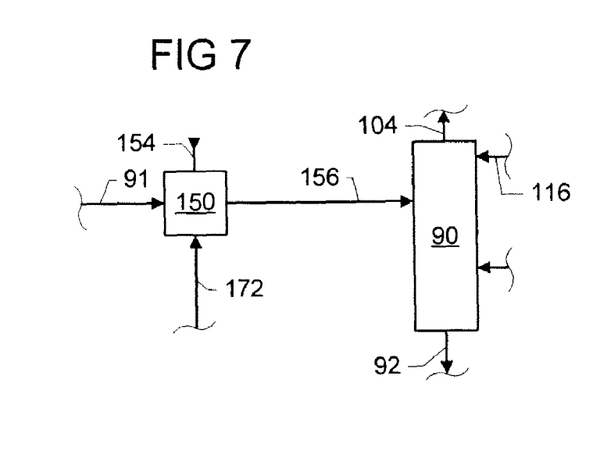

FIG. 6 shows a variation of FIG. 2 where the isomerization reaction zone effluent in line 72 passes to cooler 158 which condenses the butanes and propane to produce a partially condensed stream that passes via line 162 to separator 160. Separator 160 separates, by flashing for example, the stream into a gas phase and a liquid phase and advantageously concentrates in the liquid phase components that are desired for passing to chloride treater 150. Separator 160 can be a flash drum. The liquid phase contains butane, propane, and dissolved hydrogen chloride and passes via line 172 to chloride treater 150, where olefins introduced via line 154 react with hydrogen chloride to produce chloroparaffins. The chloride treater effluent in line 156 and the overhead liquid slip stream in line 91 pass to depropanizer 90. The gas phase from separator 160 contains hydrogen, could interfere with the chlorination reactions in chloride treater 150, and is routed via line 164 to conventional gas recovery facilities. FIG. 7 shows a variation of FIG. 6 in which not only the liquid phase in line 172 passes to chloride treater 150 but the isostripper overhead liquid in line 91 also flows to chloride treater 150.

The embodiments in FIGS. 8 to 13 use an alkylation reaction zone effluent flash 170. Flash zone 170 can be any suitable type which are conventional and well known. Flashing the alkylation reaction zone effluent can be advantageous and an efficient way of separating isobutane from the alkylation effluent for recycling to the alkylation reactor. Alkylation reaction zone effluent in line 16 passes to flash zone 170. A liquid stream depleted in isobutane flows from flash zone 170 via line 166 and combines with the net bottoms stream in line 41 from reactivation stripper 40, and the combined stream flows via line 48 to isostripper 50. An overhead vapor stream enriched in isobutane and containing propane and lighter hydrocarbons, hydrogen chloride, and possibly molecular hydrogen exits via line 175 from flash zone 170. A portion of the overhead liquid in line 175 flows via line 176 and combines with the isobutane-containing net isostripper overhead liquid in line 178 to form the recycle stream in line 132. The recycle stream thus contains mainly isobutane but it can also contain propane and possibly hydrogen chloride. After the overhead stream in line 175 is compressed and condensed, most of the overhead condensed liquid stream in line 175 from flash zone 170 is recycled to alkylation reactor assembly 10 and a slip stream of overhead condensed liquid passes via lines 174 and 152 to depropanizer 90 to prevent propane and lighter hydrocarbons from accumulating to unacceptable levels in the process. Before entering depropanizer 90 this slip stream combines with the isomerization reaction zone effluent in line 72.

Figure 8:
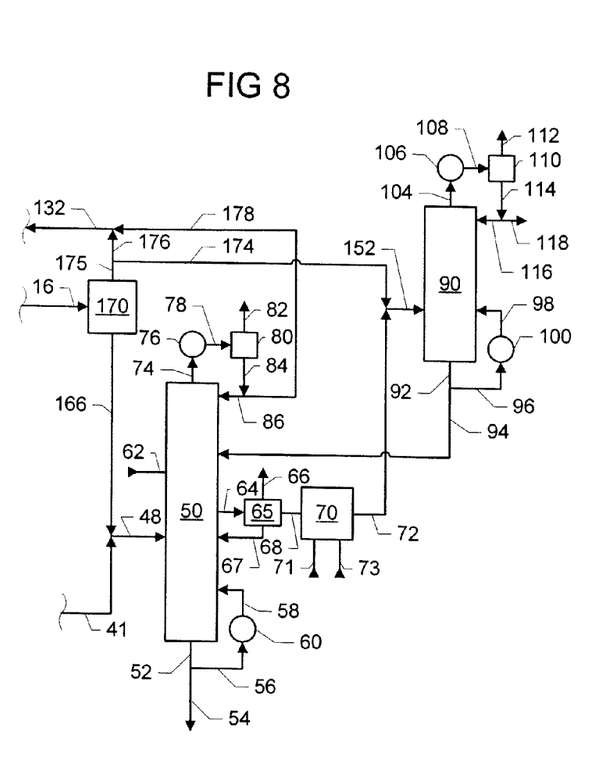
Figure 9:
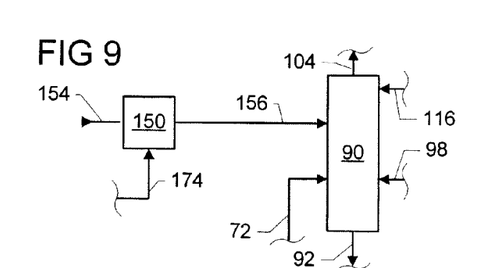

The embodiments in FIGS. 9 to 13 use a chloride treater 150 fed by an olefin-containing stream in line 154 as described previously. FIG. 9 shows a variation of FIG. 8. The flash overhead condensed liquid containing hydrogen chloride in line 174 flows to chloride treater 150. A treater effluent stream containing chloroparaffins and propane and lighter paraffins passes via line 156 to depropanizer 90. The chloroparaffins are carried in the net depropanizer bottoms stream via line 94 to isostripper 50, and are recycled to the alkylation reactor assembly 10 via lines 178 and 132.

Figure 10:
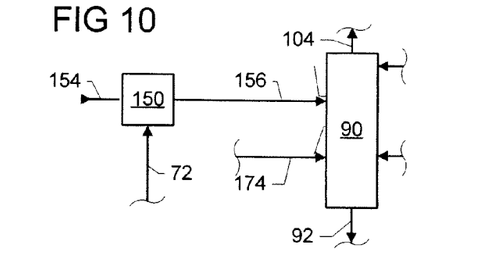
Figure 11:
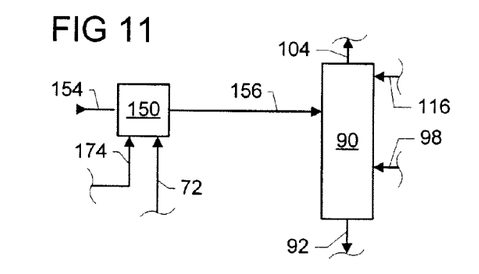

FIG. 10 shows another variation of FIG. 8. The isomerization reaction zone effluent in line 72, rather than the flash overhead condensed liquid as in FIG. 9, flows to chloride treater 150. The treater effluent stream in line 156 and the flash overhead condensed liquid slip stream in line 174 flow to depropanizer 90. FIG. 11 shows yet another variation of FIG. 8 in which both the flash overhead condensed liquid slip stream in line 174 and the isomerization reaction zone effluent in line 72 flow to chloride treater 150.

Figure 12:
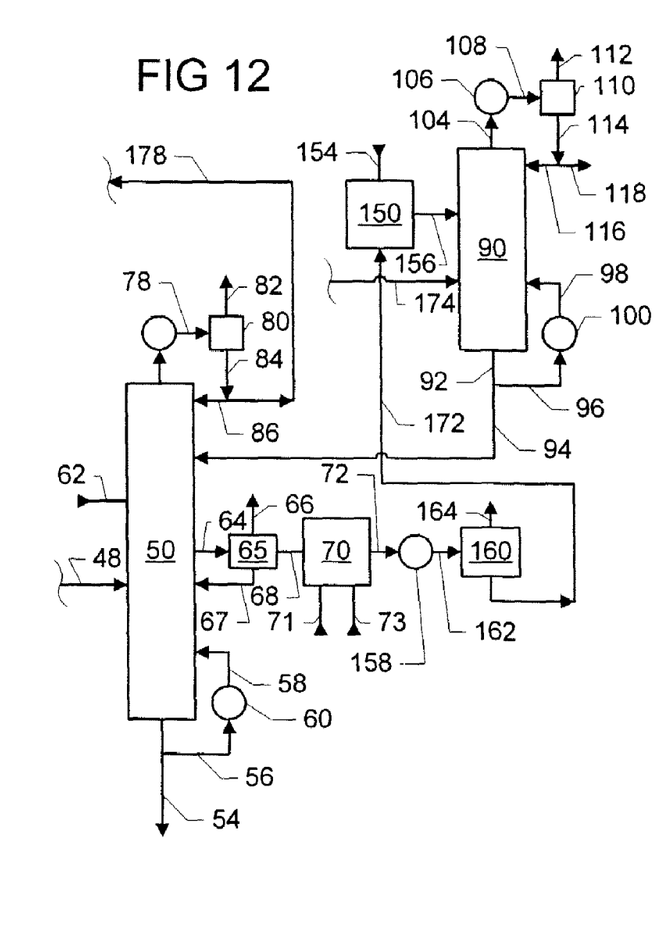
Figure 13:
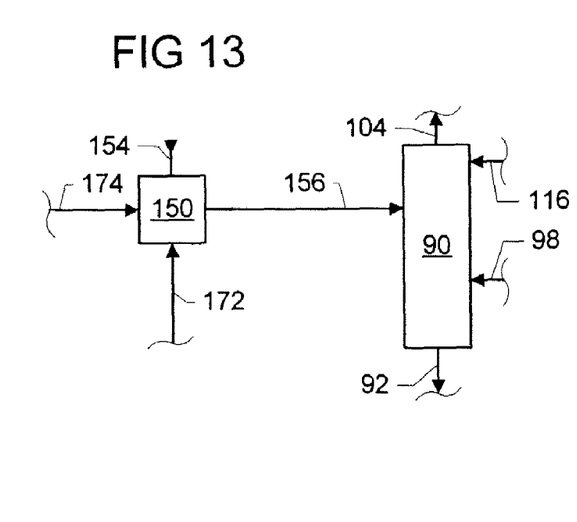

FIG. 12 shows a variation of FIG. 8 that uses a cooler 158 and a separator 160 for the isomerization reaction zone effluent as described previously. The liquid phase in line 172 passes to chloride treater 150. The chloride treater effluent in line 156 and the flash overhead condensed liquid slip stream in line 174 pass to depropanizer 90. FIG. 13 shows a variation of FIG. 12 in which not only the liquid phase in line 172 passes to chloride treater 150 but the slip stream of flash overhead condensed liquid in line 174 also flows to chloride treater 150.

The alkylation catalyst is not critical to the broad aspects of the process disclosed herein, and any suitable alkylation catalyst may be used. The alkylation catalyst typically is solid, heterogeneous, and stable and has the required activity and selectivity for the desired reaction at the alkylation conditions. Alkylation catalysts are described, for example, in U.S. Pat. No. 2,999,074; U.S. Pat. No. 3,318,820; U.S. Pat. No. 4,384,161; U.S. Pat. No. 4,935,577; U.S. Pat. No. 5,157,200; U.S. Pat. No. 5,157,196; and U.S. Pat. No. 5,986,158. The alkylation catalyst typically contains a solid acid constituent. The alkylation catalyst can be amorphous (e.g., based upon an amorphous inorganic oxide), crystalline (e.g., based upon a crystalline inorganic oxide), or a mixture of both. A catalyst containing a crystalline inorganic oxide would still normally contain an amorphous matrix or binder. The crystalline inorganic oxide can be a molecular sieve or a non-molecular sieve, or a mixture of a molecular sieve and a non-molecular sieve can be used. The molecular sieve can be zeolitic or non-zeolitic, or a mixture of a zeolite and a non-zeolite can be used. The alkylation catalyst can comprise a halide component or can be catalytically promoted by a halide component, such as a chloride component. For example, the alkylation catalyst can contain a mineral acid or a mixture of mineral acid and Friedel-Crafts metal halide promoter, where the metal may be aluminum, zirconium, tin, tantalum, gallium, antimony, boron, or mixtures thereof, and the halide may be fluoride, chloride, bromide, or mixtures thereof. In another example, the alkylation catalyst can contain or have been treated with a Lewis acid, such as boron trifluoride, aluminum chloride, antimony pentafluoride, or mixtures thereof. In another example, the catalyst can contain a zeolite such as ZSM-4, ZSM-3, X, Y, mordenite, beta, MCM-22, MCM-36, or mixtures thereof. In another example, the catalyst can contain silicate, aluminophosphate, silicoaluminophosphate, alumina (e.g., anhydrous gamma-alumina), silica, silica-alumina, sulfated oxide (e.g., sulfated oxide of zirconium, molybdenum, titanium, tungsten, tin, or mixtures thereof), or mixtures thereof. In another example, the matrix or binder can contain alumina, silica, clay, titania, zirconia, boria, aluminophosphate, or mixtures thereof. In another example, the alkylation catalyst can comprise an alkali metal cation, an alkaline earth metal cation, or mixtures thereof. The alkylation catalyst can comprise a hydrogenation function such as one or more transition metal element components comprising an element from Groups 8-10 of the periodic table, such as platinum, palladium, or mixtures thereof. The alkylation catalyst may be in the form of any suitable shape and size.

Contacting within the alkylation reaction zone may be effected using the alkylation catalyst in a fixed-bed system, a moving-bed system, a fluidized-bed system, or in a batch-type operation. Transport reactors and/or ebulliated bed reactors are preferred. In a transport reactor the catalyst bed as a whole moves, and when the direction of catalyst flow is upward the transport reactor is often called a riser-reactor. In a common arrangement, the isoparaffin reactant can engage a solid alkylation catalyst at the bottom of the riser-reactor and transports the catalyst in a fluidized state upward. A stream of catalyst and alkylate, alkylation by-products, and unreacted isoparaffin can discharge from the top of the riser-reactor into a separation zone. The hydrocarbons and the catalyst disengage, with the hydrocarbons being withdrawn overhead for recovery and the catalyst dropping by gravity to the bottom of the separation zone. Some of the catalyst that collects in the separation zone typically has enough residual activity that it can be reused in the riser-reactor without first being regenerated. Such still-active catalyst can be recirculated to the bottom of the riser-reactor. The introduction of reactants and catalyst to the bottom of the riser-reactor can be controlled by any suitable means, including slide valves, other types of valves, lock hoppers, fluid flow control (reverse flow of liquid), screw conveyors, and L-valves. Suitable alkylation reaction zones are described in, for example, U.S. Pat. No. 5,672,798; U.S. Pat. No. 6,172,274 B1; U.S. Pat. No. 6,392,114 B1; and U.S. Pat. No. 6,814,943 B2.

The alkylation conditions depend mainly on the reactants, the alkylation catalyst, and the alkylation reaction zone. The reactants may be in the liquid phase, a mixed liquid-vapor phase, or a vapor phase when contacted with the catalyst particles, with excellent results being obtained by application of the present invention to a primarily liquid-phase operation. The alkylation reaction zone may comprise a single reactor or two or more separate reactors with suitable means to ensure that the desired alkylation temperature is maintained at the entrance to each reactor. In general suitable operating conditions for the alkylation reaction zone include a temperature of from about −50° C. (−58° F.) to about 100° C. (212° F.), typically from about 0° C. (32° F.) to about 100° C. (212° F.). Reactor operating pressures are generally as required to maintain at least a portion of the hydrocarbons present as a liquid. The pressure may range from about 1380 kPa(g) (200 psi(g)) to about 4830 kpa(g) (700 psi(g)), often from about 3100 kPa(g) (450 psi(g)) to about 4140 kPa(g) (600 psi(g)). In a riser-reactor, the weight ratio of catalyst per olefin is generally from about 3 to about 10, the liquid residence time is in the general range of from about 60 to about 150 seconds, and the catalyst residence time is in the general range of from about 90 to about 300 seconds. The riser-reactor is preferably designed and operated in a manner intended to promote plug flow (minimal backmixing) of the reactants, products, and catalyst within the riser-reactor. However, the liquid flows upward faster than the catalyst in order to transport it. The alkylation reactor is usually operated with a stoichiometric excess of the isoparaffin compared to the alkylating agent. The molar ratio of the isoparaffin to olefin at the alkylation reactor inlet is typically greater than 2:1 and often greater than 8:1. Ratios of 10:1 or higher can be used, but ratios of about 100:1 or higher are generally considered to be uneconomical unless the catalyst system allows operation with direct recycle of alkylation reactor effluent to the inlet of the alkylation reactor. Injection of the olefin at a number (generally 4 or more) of points along the flow path of the isoparaffin through the alkylation reactor may be employed to maintain a higher average isoparaffin to olefin ratio and/or to maintain reactants in the alkylation reaction zone in the preferred liquid phase.

Provisions may be made to remove used catalyst from the process and to replace the used catalyst with fresh catalyst. Conventional-valved lock hopper systems may be used for this purpose. Alkylation catalyst, especially catalyst that has been deactivated, can be withdrawn from the alkylation reaction zone or from any suitable point in a catalyst flow cycle loop, subjected to regeneration, and returned to the zone or loop. Regeneration conditions depend mainly on the nature of the deactivation, the desired extent of reactivation, the alkylation catalyst, and the catalyst regeneration zone. Regeneration systems are described in U.S. Pat. No. 6,392,114 B1, for example.

The alkylation reaction zone effluent generally also contains the desired product of alkylation (alkylate), byproducts of side reactions, and unreacted feedstock. For example, in a process for the production of motor fuel by alkylating butenes with isobutane, the alkylate comprises hydrocarbons having generally from 6 to 12 carbon atoms per molecule and preferably 8 carbon atoms per molecule. However, in addition to unreacted or excess isobutane, the alkylation reaction zone effluent can comprise hydrocarbons having from 1 to 12 carbon atoms per molecule, including methane, ethane, propane, propene, butanes, butenes, pentanes, pentenes, hexanes, heptanes, octanes, nonanes, decanes, undecanes, and dodecanes. It is a requirement that the alkylation reaction zone effluent contains at least one "$C_3$-minus paraffin", which as used herein means a paraffin component having 3 or less carbon atoms per molecule, namely methane, ethane, or propane. The alkylation reaction zone effluent can also contain a hydrogen halide. For example, if chloride is present on the alkylation catalyst or a chloride component such as an organic chloride is used as a catalytic promoter, the effluent of the alkylation zone will likely contain a chloride-containing compound, such as hydrogen chloride. If present in the alkylation reaction zone effluent, the hydrogen halide has a concentration of typically greater than about 250 wt-ppm and usually from about 1000 to about 10000 wt-ppm. However, the process disclosed herein is useful with concentrations higher or lower than these ranges. The alkylation reaction zone effluent may contain organic halides, which typically include the products of halogenating the alkylating agent, such as propyl chlorides and butyl chlorides. The alkylation reaction zone effluent can contain molecular hydrogen, but typically there is little or none.

To improve separation and recovery of the components in the alkylation reaction zone effluent, the alkylation reaction zone effluent can be flashed. As used herein, flashing the alkylation reaction zone effluent means that the pressure of the alkylation reaction zone effluent is lowered from the alkylation reaction pressure. Flashing of the alkylation reaction zone effluent is optional. Flashing is conventional and well known and any suitable flashing conditions can be used. Flashing may occur at constant enthalpy or the enthalpy of the alkylation reaction zone effluent may change. Flashing can occur in a single step or in multiple steps. Since the hydrocarbons in the alkylation reaction zone effluent are usually in a liquid phase, the flashing typically vaporizes some of the lighter hydrocarbons in the effluent, such as the isoparaffin. The resulting alkylation reaction zone effluent may thus be a two-phase mixture of vapor and liquid. Flashing also typically lowers the temperature of the alkylation reaction zone effluent.

After flashing, the alkylation reaction zone effluent can be phase separated prior to passing to a debutanizer distillation zone described hereinafter. Phase separation is optional. Phase separation is conventional and well known and any suitable phase-separation conditions may be used. Phase separation after flashing of the alkylation reaction zone effluent takes place at a pressure of generally from about 0 kPa(g) (0 psi(g)) to about 483 kpa(g) (70 psi(g)) and at a temperature of generally from about −9° C. (15° F.) to about 32° C. (90° F.). (The pressure could also be subatmospheric, provided that suitable measures to limit or prevent air ingress are taken. However, such measures are usually impractical or uneconomical.) The phase separation conditions depend in part on the number of times (if any) the liquid phase derived therefrom is flashed enroute from the alkylation reactor to a debutanizer distillation zone. Each stage of flashing of liquid derived from an upstream phase separation typically lowers the pressure and temperature of the liquid that is flashed, and generally the greater the number of stages, the smaller is the drop in pressure and temperature from stage to stage. For example, if the alkylation reaction zone effluent is flashed, phase-separated, and the derived liquid flows without further flashing to a debutanizer distillation zone, the phase separation occurs at a pressure of generally from about 69 kPa(g) (10 psi(g)) to about 207 kPa(g) (30 psi(g)) and at a temperature of generally from about 7° C. (45° F.) to about 18° C. (65° F.). However, if the liquid derived from the phase separation is itself flashed and phase-separated, the phase separation of the derived liquid is typically done at the conditions given above while the phase separation of the alkylation reaction zone effluent occurs at a higher pressure and temperature, generally from about 207 kPa(g) (30 psi(g)) to about 414 kPa(g) (60 psi(g)) and generally from about 7° C. (45° F.) to about 24° C. (75° F.).

The vapor phase that is derived from phase-separating the flashed alkylation reaction zone effluent, and each vapor phase derived from phase-separating each flashed derived liquid, is enriched in the isoparaffin, the $C_3$-minus paraffin, and if present the hydrogen halide relative to the reaction zone effluent. Each derived liquid phase is depleted in each of those components if present. Although each derived vapor phase may be recycled separately to the alkylation reaction zone, it is more efficient to compress the relatively low-pressure derived vapor phase(s) as required and combine them with the highest-pressure derived vapor phase to form a single stream that is subject to further processing. Any or all of the derived vapor phase(s) may be condensed.

The alkylation reaction zone effluent, or the liquid phase(s) derived from flashing and phase-separation as described above, pass to a debutanizer distillation zone. The debutanizer distillation zone removes the isoparaffin and the halogen-containing species from the alkylate. Although the debutanizer distillation zone may comprise a distillation column that has either a rectification section without a stripping section or a stripping section without a rectification section, preferably the debutanizer distillation zone preferably has both rectification and stripping sections. If the debutanizer distillation zone has an optional side draw for separately recovering normal butane and the side draw contains heavy components then the side draw can pass to an optional rectifier to remove such heavy components for their return to the debutanizer distillation zone. Makeup field butanes are typically passed to debutanizer distillation zone. A bottoms stream from a depropanizer distillation zone described hereinafter can pass to the debutanizer distillation zone. The trays in the rectification and/or stripping sections of the debutanizer distillation zone can be of any suitable type and number, and the operating conditions of the debutanizer distillation zone can be of any suitable range to effect the desired separation. For example, the bottoms temperature can be from about 325° F. (163° C.) to about 425° F. (218° C.), the overhead temperature can be from about 120° F. (49° C.) to about 160° F. (71° C.), the pressure can be from about 120 psi(g) (827 kPa(g)) to about 200 psi(g) (1379 kPa(g)). The overhead stream of the debutanizer distillation zone typically contains a $C_3$-minus paraffin and can contain a hydrogen halide (e.g., hydrogen chloride).

A portion of the overhead stream of the debutanizer distillation zone or a portion of the vapor phase recovered from flashing the alkylation reaction zone effluent is compressed, is condensed, and passes to a depropanizer distillation zone. The depropanizer distillation zone separates $C_3$-minus paraffin, such as methane, ethane, and propane, and molecular hydrogen from the portion of the overhead stream or the vapor phase and removes the $C_3$-minus paraffin in a depropanizer overhead stream. The depropanizer bottom stream can contain isoparaffin (e.g., isobutane) and chloroparaffins and can be recycled to the debutanizer distillation zone. The depropanizer distillation zone typically has both a rectification and a stripping section. The trays in the rectification and/or stripping sections of the depropanizer distillation zone can be of any suitable type and number, and the operating conditions of the depropanizer distillation zone can be of any suitable range to effect the desired separation. For example, the bottoms temperature can be from about 93° C. (200° F.) to about 121° C. (250° F.), the overhead temperature can be from about 38° C. (100° F.) to about 93° C. (200° F.), the pressure can be from about 1379 kPa(g) (200 psi(g)) to about 2413 kPa(g) (350 psi(g)).

When it is desired to recover chlorides from the portion of the overhead stream of the debutanizer distillation zone or from a portion of the vapor phase recovered from flashing the alkylation reaction zone effluent using a chloride treater upstream of the depropanizer distillation zone, it may be desirable to at least partially condense either stream so that the chloride treater operates in at least a partial liquid phase or essentially entirely in the liquid phase. An essentially all vapor phase may also be desirable.

Normal paraffins pass to the isomerization reaction zone. The normal paraffin feedstock together with a side draw, if any, recovered from the debutanizer distillation zone is fed to the isomerization reaction zone. Thus, the isomerization feed may contain normal paraffin or isoparaffin recycled from the effluent of the isomerization reaction zone. The isomerization feed preferably contain low concentrations of unsaturated hydrocarbons (e.g., up to 10 wt-%) and hydrocarbons having more than 4 carbon atoms per molecule (e.g., up to 20 wt-%) to restrict hydrogen consumption and cracking reactions. In the isomerization reaction zone the isomerization feed is subjected to isomerization conditions including the presence of isomerization catalyst preferably in the presence of a limited amount of hydrogen. The isomerization of normal butane is generally considered reversible first order reactions. Thus, the isomerization reaction zone effluent will contain a greater concentration of isoparaffin and a lesser concentration of normal paraffin than does the isomerization feed. In one embodiment of the process disclosed herein, the isomerization conditions are sufficient to isomerize at least about 20, preferably, between 30 and 60, mass-% of the normal paraffins in the isomerization feed. In general, the isomerization conditions achieve at least about 70, preferably at least about 75, say, 75 to essentially 100, percent of equilibrium for $C_4$ paraffins present in the isomerization feed. In many instances, the isomerization reaction zone effluent has a mass ratio of isoparaffin to normal butane of at least about 1.2:1, preferably between about 1.4 to 2:1.

The isomerization catalyst is not critical to the broad aspects of the process disclosed herein, and any suitable isomerization catalyst may find application. Suitable isomerization catalysts include acidic catalysts using chloride for maintaining the sought acidity. The isomerization catalyst can be amorphous (e.g., based upon an amorphous inorganic oxide), crystalline (e.g., based upon a crystalline inorganic oxide), or a mixture of both. A catalyst containing a crystalline inorganic oxide would still normally contain an amorphous matrix or binder. The crystalline inorganic oxide can be a molecular sieve or a non-molecular sieve, or a mixture of a molecular sieve and a non-molecular sieve can be used. The molecular sieve can be zeolitic or non-zeolitic, or a mixture of a zeolite and a non-zeolite can be used. The catalyst may comprise platinum on mordenite, aluminum chloride on alumina, and platinum on sulfated or tungstated metal oxides such as zirconia. The catalyst may comprise a platinum group metal such as platinum on a chlorided alumina base, such as an anhydrous gamma-alumina with a high degree of purity. The chloride component of the isomerization catalyst, termed in the art "a combined chloride", is present in an amount from about 2 to about 10 wt-%, preferably from about 5 wt-% to about 10 wt-%.

Contacting within the isomerization reaction zone may be effected using the catalyst in a fixed-bed system, a moving-bed system, a fluidized-bed system, or in a batch-type operation. A fixed-bed system is preferred. The reactants may be contacted with the bed of catalyst particles in upward, downward, or radial-flow fashion. The reactants may be in the liquid phase, a mixed liquid-vapor phase, or a vapor phase when contacted with the catalyst particles, with excellent results being obtained by application of the present invention to a primarily vapor-phase operation. The isomerization reaction zone may be in a single reactor or in two or more separate reactors with suitable means to ensure that the desired isomerization temperature is maintained at the entrance to each zone. Two or more reactors in sequence are preferred to enable improved isomerization through control of individual reactor temperatures and for partial catalyst replacement without a process shutdown. Suitable isomerization reaction zones with separator and recycle gas compressor are described for butane isomerization in chapter 5.4, "UOP Butamer Process" of the earlier edition of the Handbook, namely Handbook of Petroleum Refining Processes, edited by Robert A. Meyers, McGraw-Hill, New York, 1986, ISBN 0-07-041763-6. Suitable isomerization reaction zones without separator and recycle gas compressor are described for butane isomerization in chapter 9.2 "UOP Butamer Process" of the Handbook. Isomerization processes without hydrogen recycle are described in U.S. Pat. No. 4,804,803; U.S. Pat. No. 4,929,794; and U.S. Pat. No. 5,026,950. Additional information on pentane isomerization is in chapter 5.1 "UCC Total Isomerization Process (TIP)" and chapter 5.5 "UOP Penex Process" of the earlier edition of the Handbook and in chapter 9.3 "UOP Penex Process" of the Handbook. The teachings of these references are hereby incorporated herein by reference.

Isomerization conditions in the isomerization zone include reactor temperatures usually ranging from about 40° C. (104° F.) to about 250° C. (482° F.). Lower reaction temperatures are generally preferred in order to favor equilibrium mixtures having the highest concentration of isoparaffin (e.g., isobutane) and to minimize cracking of the feed to lighter hydrocarbons. Temperatures in the range of from about 100° C. (212° F.) to about 200° C. (392° F.) are preferred in the process disclosed herein. Reactor operating pressures generally range from about 100 kpa(a) (14.5 psi(a)) to about 10 MPa(a) (1450 psi(a)), preferably between about 0.5 MPa(a) (72.5 psi(a)) and about 4 MPa(a) (580 psi(a)). Liquid hourly space velocities range from about 0.2 to about 25 volumes of isomerizable hydrocarbon feed per hour per volume of catalyst, with a range of about 0.5 to 15 $hr^{-1}$ being preferred.

Hydrogen is admixed with or remains with the feed to the isomerization zone to provide a mole ratio of hydrogen to hydrocarbon feed of from about 0.01 to 20. The hydrogen may be supplied totally from outside the process or supplemented by hydrogen recycled to the feed after separation from isomerization reaction zone effluent. Light hydrocarbons and small amounts of inerts such as nitrogen and argon may be present in the hydrogen. Water should be removed from hydrogen supplied from outside the process, preferably by an adsorption system as is known in the art. In a preferred embodiment the hydrogen to hydrocarbon mol ratio in the reaction zone effluent is equal to or less than 0.05, generally obviating the need to recycle hydrogen from the reaction zone effluent to the feed.

When a chlorided catalyst is used, operation of the isomerization reaction zones often uses a small amount of a chloride promoter. The chloride promoter, typically an organic chloride, serves to maintain a high level of active chloride on the catalyst as low levels are continuously stripped off the catalyst by the hydrocarbon stream passed to the isomerization reaction zone. The promoter in the isomerization reaction zone is maintained such that the concentration of promoter is from about 50 to about 500 wt-ppm in the isomerization reaction zone effluent. The preferred promoter compound is carbon tetrachloride. Other suitable promoter compounds include oxygen-free decomposable organic chlorides such as propyldichloride, butylchloride, and chloroform to name only a few of such compounds. The need to keep the reactants passed to isomerization reaction zone dry is reinforced by the presence of the organic chloride compound which may convert, in part, to hydrogen chloride. As long as the process streams are kept dry, there will be no adverse effect from the presence of small amounts of hydrogen chloride.

The isomerization reaction zone effluent typically contains a mixture of isoparaffins and normal paraffins. For paraffins having the same carbon number, the isoparaffins and normal paraffins are near their equilibrium concentrations at the isomerization conditions. Because of side reactions, the isomerization reaction zone effluent can contain at least one $C_3$-minus paraffin, such as methane, ethane, and propane. The $C_3$-minus paraffin in the isomerization reaction zone effluent may have the same number of carbon atoms per molecule as does the $C_3$-minus paraffin in the alkylation reaction zone effluent, but not necessarily. In addition, especially where a chloride promoter or a chlorided catalyst is used for isomerization, the isomerization reaction zone effluent can contain a chloride component or is distilled or stripped to remove the chloride components as well as light ends. The concentration of promoter, typically in the form of hydrogen chloride, in the isomerization reaction zone effluent is usually from about 50 to about 500 wt-ppm.

In the process disclosed herein, whether operating with one or more isomerization reactors, the effluent from the isomerization reaction zone or components in the isomerization reaction effluent enters the same separation zone (e.g., a depropanizer distillation zone), previously described, into which the purge (or slip-stream) containing components from the alkylation reaction zone effluent passes. In the separation zone, the isoparaffin (e.g., isobutane) is separated by distillation from both the $C_3$-minus paraffin from the alkylation reaction zone effluent and the $C_3$-minus paraffin from the isomerization reaction zone effluent. If present in the streams fed to the separation zone, hydrogen and light olefins may also be separated from the isoparaffin. Chloroparaffins and components heavier than the isoparaffin are withdrawn from the depropanizer distillation zone in a bottoms stream passed to the debutanizer distillation zone.

In a preferred embodiment, a flash zone may be located between the isomerization reaction zone and the depropanizer distillation zone to separate hydrogen and other light gases from most of the hydrogen chloride in the isomerization reaction zone effluent. The hydrogen and light gases are recovered in the flash overhead, which is relatively free of chloride and may be vented from the process without any significant loss of chloride. The hydrogen chloride is recovered in the flash bottoms stream which is routed to the depropanizer distillation zone.

Flashing the isomerization reaction zone effluent is preferred when it is desired to recover chlorides from the isomerization reaction zone effluent using a chloride treater upstream of the depropanizer distillation zone. Flashing removes hydrogen and light gases, allows the chloride treater to operate in the liquid phase, and prevents hydrogen from reacting with the olefins fed to the chloride treater. The depropanizer distillation zone bottoms stream contains most of the chloroparaffins produced in the chloride treater and passes to the debutanizer distillation zone.

All references herein to the groups of elements of the periodic table are to the IUPAC "New Notation" on the Periodic Table of the Elements in the inside front cover of the book titled CRC Handbook of Chemistry and Physics, ISBN 0-8493-0480-6, CRC Press, Boca Raton, Fla., U.S.A., 80th Edition, 1999-2000.

The invention claimed is:

1. An alkylation process comprising:
  a) producing an alkylate and forming a first $C_3$-minus paraffin from isobutane and a $C_3$-$C_4$ olefin, and forming an alkylate-containing stream comprising the alkylate, isobutane, and the first $C_3$-minus paraffin;
  b) separating by distillation in a first distillation zone the alkylate from isobutane and the first $C_3$-minus paraffin;
  c) recycling at least a portion of the isobutane separated in step b) to step a), wherein steps a), b), and c) define a flow cycle loop;
  d) at least intermittently withdrawing a purge comprising the first $C_3$-minus paraffin from at least one point in the flow cycle loop;

e) producing isobutane and forming a second $C_3$-minus paraffin from normal butane, and forming an isomerate stream comprising isobutane and the second $C_3$-minus paraffin;

f) separating by distillation in a second distillation zone isobutane from the first C3-minus paraffin and the second $C_3$-minus paraffin; and g) passing at least a portion of the isobutane separated in step f) to at least one point in the flow cycle loop; wherein the $C_3$-$C_4$ olefin is a first $C_3$-$C_4$ olefin, wherein the purge comprises hydrogen chloride, and wherein the process further comprises reacting at least a portion of the hydrogen chloride in the purge with a second $C_3$-$C_4$ olefin in a treating zone to produce a $C_3$-$C_4$ chloroparaffin, separating by the distillation in step f) the $C_3$-$C_4$ chloroparaffin produced in the treating zone from the first $C_3$-minus paraffin and the second $C_3$-minus paraffin, and passing at least a portion of the $C_3$-$C_4$ chloroparaffin separated in step f) to at least one point in the flow cycle loop.

2. The process of claim 1 wherein the alkylate is produced in step a) in the presence of a solid alkylation catalyst containing chloride.

3. The process of claim 1 wherein the isomerate stream comprises hydrogen chloride and wherein the process further comprises passing at least a portion of the hydrogen chloride in the isomerate stream to the treating zone.

4. The process of claim 1 wherein the $C_3$-$C_4$ olefin is a first $C_3$-$C_4$ olefin, wherein the isomerate stream comprises hydrogen chloride, and wherein the process comprises reacting at least a portion of the hydrogen chloride in the isomerate stream with a second $C_3$-$C_4$ olefin in a treating zone to produce a $C_3$-$C_4$ chloroparaffin, separating by the distillation in step f) the $C_3$-$C_4$ chloroparaffin produced in the treating zone from the first $C_3$-minus paraffin and the second $C_3$-minus paraffin, and passing at least a portion of the $C_3$-$C_4$ chloroparaffin separated in step f) to at least one point in the flow cycle loop.

5. The process of claim 4 wherein the isobutane is produced in step e) in the presence of an isomerization catalyst containing chloride.

6. The process of claim 4 wherein the isomerate stream comprises molecular hydrogen, wherein the process further comprises separating by flashing molecular hydrogen from hydrogen chloride and isobutane, and wherein the at least a portion of the hydrogen chloride in the isomerate stream comprises at least a portion of the hydrogen chloride separated by the flashing.

7. The process of claim 6 wherein the purge comprises hydrogen chloride and wherein the process further comprises passing at least a portion of the hydrogen chloride in the purge to the treating zone.

8. The process of claim 1 wherein the alkylate-containing stream comprises hydrogen chloride and wherein the process further comprises separating by the distillation in step b) isobutane from hydrogen chloride.

9. The process of claim 8 wherein the purge comprises isobutane separated by the distillation in step b).

10. The process of claim 8 wherein the $C_3$-$C_4$ olefin is a first $C_3$-$C_4$ olefin and wherein the process further comprises reacting at least a portion of the hydrogen chloride separated in step b) with a second $C_3$-$C_4$ olefin in a treating zone to produce a $C_3$-$C_4$ chloroparaffin, separating by the distillation in step f) the $C_3$-$C_4$ chloroparaffin produced in the treating zone from the first $C_3$-minus paraffin and the second $C_3$-minus paraffin, and passing at least a portion of the $C_3$-$C_4$ chloroparaffin separated in step f) to at least one point in the flow cycle loop.

11. The process of claim 10 wherein the isomerate stream comprises hydrogen chloride and wherein the process further comprises passing at least a portion of the hydrogen chloride in the isomerate stream to the treating zone.

12. The process of claim 11 wherein the isomerate stream comprises molecular hydrogen, wherein the process further comprises separating by flashing molecular hydrogen from hydrogen chloride and isobutane, and wherein the at least a portion of the hydrogen chloride in the isomerate stream comprises at least a portion of the hydrogen chloride separated by the flashing.

13. The process of claim 1 wherein the process further comprises flashing at least a portion of the alkylate-containing stream and wherein the distillation in step b) comprises a countercurrent contacting distillation.

14. The process of claim 1 wherein the process further comprises separating by flashing in a flashing zone the first $C_3$-minus paraffin from isobutane and the alkylate, wherein the purge comprises the first $C_3$-minus paraffin separated by the flashing, and wherein the distillation in step b) comprises a countercurrent contacting distillation.

15. The process of claim 1 wherein the process further comprises separating by the distillation in step b) normal butane from isobutane and wherein the normal butane from which isobutane is produced in step e) comprises at least a portion of the normal butane separated in step b).

16. The process of claim 15 wherein the process further comprises withdrawing a portion of the normal butane separated in step b) from the process.

17. An alkylation process comprising:

a) alkylating isobutane with a $C_3$-$C_4$ olefin in an alkylation reaction zone containing a solid alkylation catalyst at alkylation conditions sufficient to provide an alkylation effluent comprising alkylate, isobutane, and a first $C_3$-minus paraffin;

b) distilling in a debutanizer distillation zone at least a portion of the alkylation effluent into a debutanizer overhead comprising isobutane and a debutanizer bottoms stream comprising the alkylate;

c) recycling at least a portion of the debutanizer overhead to the alkylation reaction zone, wherein steps a), b), and c) define a flow cycle loop;

d) at least intermittently withdrawing a purge comprising the first $C_3$-minus paraffin from at least one point in the flow cycle loop;

e) isomerizing normal butane in an isomerization reaction zone containing an isomerization catalyst at isomerization conditions sufficient to provide an isomerization effluent comprising isobutane and a second $C_3$-minus paraffin;

f) distilling in a depropanizer distillation zone at least a portion of the purge and at least a portion of the isomerization effluent into a depropanizer overhead comprising the first $C_3$-minus paraffin and the second $C_3$-minus paraffin and a depropanizer bottoms stream comprising isobutane; and g) passing at least a portion of the depropanizer bottoms stream to at least one point in the flow cycle loop; wherein the $C_3$-$C_4$ olefin is a first $C_3$-$C_4$ olefin, wherein the alkylation effluent comprises hydrogen chloride, wherein the purge comprises hydrogen chloride, wherein the process first comprises contacting the at least a portion of the purge with a second $C_3$-$C_4$ olefin at treating conditions sufficient to react hydrogen chloride with the second $C_3$-$C_4$ olefin to provide a treating effluent comprising a $C_3$-$C_4$ chloroparaffin, wherein the distillation in step f) comprises distilling at least a portion of the treating effluent, and wherein the depropanizer bottoms stream comprises the $C_3$-$C_4$ chloroparaffin.

18. The process of claim 17 wherein the process further comprises flashing the at least a portion of the alkylation effluent to provide a flash overhead comprising the first $C_3$-minus paraffin and a flash bottoms stream comprising isobutane and the alkylate, wherein the purge is formed from at least a portion of the flash overhead, and wherein the distillation in step b) comprises a countercurrent contacting distillation of at least a portion of the flash bottoms stream.

19. The process of claim 18 wherein the flash overhead comprises isobutane.

20. The process of claim 17 wherein the $C_3$-$C_4$ olefin is a first $C_3$-$C_4$ olefin, wherein the isomerization effluent comprises hydrogen chloride, wherein the process further comprises contacting the at least a portion of the isomerization effluent with a second $C_3$-$C_4$ olefin at treating conditions sufficient to react hydrogen chloride with the second $C_3$-$C_4$ olefin to provide a treating effluent comprising a $C_3$-$C_4$ chloroparaffin and isobutane, wherein the distillation in step f) comprises distilling at least a portion of the treating effluent, and wherein the depropanizer bottoms stream comprises the $C_3$-$C_4$ chloroparaffin.

* * * * *